(12) United States Patent
Yi

(10) Patent No.: US 10,966,668 B2
(45) Date of Patent: Apr. 6, 2021

(54) METHOD AND APPARATUS TO MEASURE BODILY FLUID AND ITS CHANGE, AND BLOOD VOLUME CHANGE

(71) Applicant: Msheaf Health Management Technologies Limited, Kowloon (HK)

(72) Inventor: Cheng Yi, Marlboro, NJ (US)

(73) Assignee: Msheaf Health Management Technologies Limited, Kowloon (HK)

( * ) Notice: Subject to any disclaimer, the term of this patent is extended or adjusted under 35 U.S.C. 154(b) by 306 days.

(21) Appl. No.: 16/004,204

(22) Filed: Jun. 8, 2018

(65) Prior Publication Data

US 2019/0200938 A1    Jul. 4, 2019

Related U.S. Application Data

(60) Provisional application No. 62/612,442, filed on Dec. 31, 2017.

(51) Int. Cl.
*A61B 5/0205* (2006.01)
*A61B 5/053* (2021.01)
*A61B 5/026* (2006.01)
*A61B 5/024* (2006.01)
*A61B 5/00* (2006.01)
*A61B 5/0295* (2006.01)
*A61B 5/0537* (2021.01)
*A61B 5/1468* (2006.01)

(52) U.S. Cl.
CPC ............ *A61B 5/7278* (2013.01); *A61B 5/024* (2013.01); *A61B 5/0205* (2013.01); *A61B 5/026* (2013.01); *A61B 5/0295* (2013.01); *A61B 5/0537* (2013.01); *A61B 5/1468* (2013.01); *A61B 5/7228* (2013.01); *A61B 5/7257* (2013.01); *A61B 2562/0214* (2013.01)

(58) Field of Classification Search
CPC ....... A61B 5/0205; A61B 5/024; A61B 5/026; A61B 5/0537; A61B 5/7203; A61B 5/7228; A61B 5/7257; A61B 5/7278; A61B 2562/0214
See application file for complete search history.

(56) References Cited

U.S. PATENT DOCUMENTS

| 2007/0043303 | A1* | 2/2007 | Osypka ............... A61B 5/7239 600/547 |
| 2015/0342497 | A1* | 12/2015 | Maktura ............. A61B 5/7275 600/547 |
| 2016/0310013 | A1* | 10/2016 | Levy .................... A61B 5/0402 |
| 2018/0143150 | A1* | 5/2018 | Bezemer ................. A61B 5/11 |

* cited by examiner

*Primary Examiner* — Thaddeus B Cox

(74) *Attorney, Agent, or Firm* — Squire Patton Boggs (US) LLP

(57) ABSTRACT

A method of calculating body fluid and blood flow in a human or animal body using multi-frequencies alternating electrical currents, determining the tissues' multi-frequency impedance and reactance changes, calculating the body fluid, blood flow and physiological parameter. With the simultaneous measurements of body's or tissues' impedance and reactance from multi-frequencies, it is possible either to compensate for the frequency-dependencies or to find the dependencies' cross relationship, and thus measure body fluid and blood flow more accurately.

16 Claims, 9 Drawing Sheets

METHOD AND APPARATUS TO MEASURE BODILY FLUID AND ITS CHANGE, AND BLOOD VOLUME CHANGE

CROSS-REFERENCE TO RELATED APPLICATIONS

The present invention claims priority to U.S. Provisional Application No. 62/612,442, filed Dec. 31, 2017, and incorporates that provisional application in its entirety by reference.

FIELD OF THE INVENTION

The present invention relates to the medical field and, in some embodiments thereof, relates to non-invasive technologies of detecting the electrical characteristics of bio-tissues and, more particularly, but not exclusively, to measurements of blood flow and body liquid levels.

BACKGROUND OF THE INVENTION

Bio-impedance and bio-reactance measurements as a non-invasive method to measure blood flow and body liquid levels have been explored widely. These technologies are well accepted in the medical fields. But they suffer some drawbacks. The measurements are frequency dependent. Some people incur different frequency-selective interference or noise than others when making the measurements. The frequency-selective impairments will result in poor measurements in some people. Even when the bodies or tissues are considered as conductance and capacitance (conductors and non-conductors), the tissues' characteristics are also frequency dependent. The tissues' integrated conductance and capacitance may not be linear along the frequency changes.

Bio-tissues are characterized as conductors and non-conductors from the electrical perspective. Conductors are measured by the conductance (reverse of resistance), non-conductors can be measured by the capacitance. Any tissue's change will be represented by changes of conductance and capacitance. The information of the above electrical characteristics can be monitored in order to detect body status.

SUMMARY OF THE INVENTION

The present invention overcomes the deficiencies of prior methods and apparatuses which use a single frequency alternating electrical current to measure bio-impedance and bio-reactance, then to calculate body fluid and cardiac outputs and their related parameters. Aspects of the present invention provide a non-invasive device and method to measure partial body's or tissues' impedance's amplitude and phase along a wide frequency range simultaneously to calculate bodily fluid and blood flow related parameters. The above parameters can be used for remote monitoring, for the diagnosis and treatment of diseases.

Multiple alternating currents of different frequencies are generated using Inverse Fast Fourier Transforms (IFFT). Multiple signals of different frequencies are summed in the frequency domain and are synchronously turned into a digital sequence in the time domain on all complete sinusoidal cycles of different frequencies using IFFTs. IFFT is similar to Orthogonal Frequency-Division Multiplexing (OFDM), in that, in one aspect, OFDM can use IFFT and/or Fast Fourier Transforms (FFTs). All of the indicated frequency signals are orthogonal to each other. The sequence length is usually a power of 2, such as $2^N$ for a sequence of N signals. The sequence can then be converted into a longer sequence, but transmitting within the same time period, a process called up-converting. In one aspect, the present invention uses up-converting to reduce quantization noise. The sequence can be stored in a memory whose contents can be output continuously or periodically by a digital controller, or generated in real-time from a digital processor. The sequence is turned into an analog current signal by a digital-to-analog converter (DAC) at fixed rates. In one aspect, the DAC clock rates are usually 100 KHz to 10 MHz. Higher clock rates will produce fewer quantization errors or distortions in the analog waveforms. As a result, the analog signal has multiple alternating currents of different frequencies.

The multiple alternating currents are then injected into a human or animal body through electrodes and form a loop with external electrical parts. When the electrical currents are passing through the body, they are modulated by the body tissues and by the changes in those tissues. There is a receiving loop which partially overlaps with the injection (transmission) loop to sample the modulated alternating currents. The sampled electrical signals and bio-signals will be amplified and analog-to-digital (A/D) converted into digital signals, which will be processed by computer processors. In one aspect, the A/D converting rate, also called the sampling rate, is usually between 100 KHz and 2.5 MHz. The sampled signals are segmented into the same time period as that of transmitted sequences, similar to an OFDM symbol. The sampled signals can be synchronized according to the injected (transmitted) signals, and be the same time period. The transmitting sequence and receiving sequence lengths shall not be necessarily the same, but the time periods should be the same and synchronized. The sampled signal sequences are then demodulated using FFTs. All signals of different frequencies are extracted. Since the transmitted signals' phases are known, they can be subtracted from the extracted signals. The apparatus system transfer equation can also be estimated offline, just like regular radio frequency (RF) equipment correction. Thus, the system amplitude and phase response can also be subtracted from the extracted signals. The final amplitudes and phases will represent the tissues' modulations, which provide the physiological information. The final signals are usually complex numbers because of human/animal tissues' modulations. The complex signals provide the human/animal tissues' information. The complex signals are processed, like low-pass filtering to remove high-frequency noise. The cutoff frequency is usually around 10 Hz. A higher cutoff frequency will bring more details of waveforms, but usually will require a higher signal-to-noise ratio (SNR).

In one aspect, the present invention has an adaptive low-pass filter. After the signal processing, the related information is extracted to calculate body fluid and blood flow parameters from different frequency signals. The results are frequency-compensated. The coefficients of equations to calculate physiological parameters are different. The cross-relationship of the results from different frequency currents also is examined. To get better results, the same physiological parameters from different frequency signals can be summed with different weights. In the information extraction process, an electrocardiogram (ECG) may be acquired as a cardio-timing reference. Blood pressure is measured separately along this processing.

Commonly calculated physiological parameters include, but are not limited to, heart rate (HR), left ventricular ejection time (LVET), stroke volume (SV), stroke index (SI), cardiac output (CO), cardiac index (CI), thoracic fluid content (TFC), velocity index (VI), acceleration index (ACI), total vascular resistance (TVR), and acceleration index (ACI).

In one aspect, the present invention provides a system that monitors hemodynamics of humans or animals, including bodily fluid and blood flow. The system includes a generator to generate alternating electrical currents of multiple frequencies; electrical transducers which can transfer the generated currents into a human or animal body, and can sense the voltage changes of the human or animal body; a plurality of sensing amplifiers, an electrical cable or a bundle of wires which connect between the electrical transducers and the generator, and between the electrical transducers and the sensing amplifiers; signal processing units which can be a single computer or a plurality of computers; and processing software and human-computer interfaces which connect a human or animal and the system. The computers can be remote, so that humans (doctors) can remotely watch the system working in a real-time mode.

Effect of the Invention

Compared to the prior art, advantages of the present invention include the following:
(1) Multi-frequency alternating stimuli (electrical currents) are used in the present invention to measure impedance and reactance, which can represent tissues' changes in many ways to achieve a more consistent and accurate result.
(2) With the measurements of body's or tissues' impedance and reactance from multi-frequencies simultaneously, the present invention can either compensate the frequency-dependencies or find the dependencies' cross relationship, make the measurements of body fluid and blood flow more accurately.

DETAILED DESCRIPTION OF EMBODIMENTS

Figure 1:
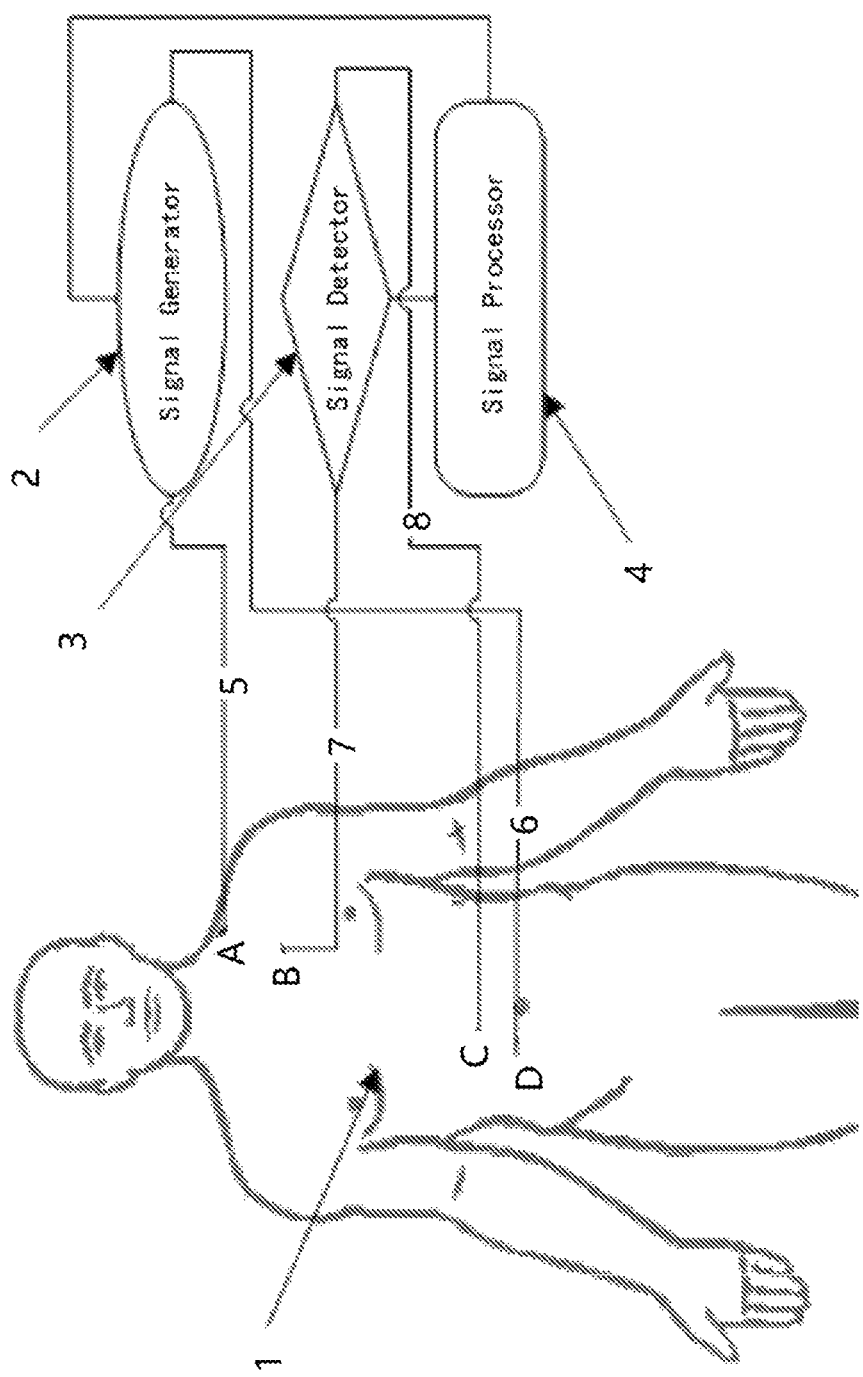
FIG. 1 is a terminal system of embodiments of the present invention.

It is to be understood that the invention is not necessarily limited in its application to the exemplary details of descriptions such as elements and directions indicated by numbers set forth in the following description and/or illustrated in the drawings and/or the Examples.

FIG. 1 shows a set-up of a terminal system on a human or animal subject. A human or animal subject 1 may have electrodes or contacts A-D to connect the human or animal subject 1 to the system. Different placements of electrodes have different focuses and measurements. For cardiovascular measurements, the placements are mainly on the thorax, along major arteries. For measurements of other organs or areas of the body, other electrode placements on the thorax, or elsewhere on the body, may be appropriate, as ordinarily skilled artisans will appreciate.

For the terminal system itself, a signal generator 2 generates a wide band signal having multiple frequency components. The system also includes a signal detector 3, a signal processor 4, and wires or cables 5-8 connecting one or more of elements 2-4 to the human or animal subject 1. Wires or cables transmit the generated signal to electrodes or contacts A and D. Electrodes A and D are placed so that the generated signals can pass through relevant arteries. In the example in FIG. 1, the electrodes A and D are connected to the thorax, through which several major arteries pass. The signal flow follows the blood flow or the arteries' longitudinal directions. The generated signals travel inside the human or animal subject 1 from A to D or from D to A. Signal detector 3 collects bio-signals from electrodes B and C through wires or cables 7 and 8. Signal processor 4 controls and coordinates signal generator 2 and signal detector 3. Signal processor 4 also processes signals received from electrodes B and C and extracts bio-information from the processed signals.

Figure 5:
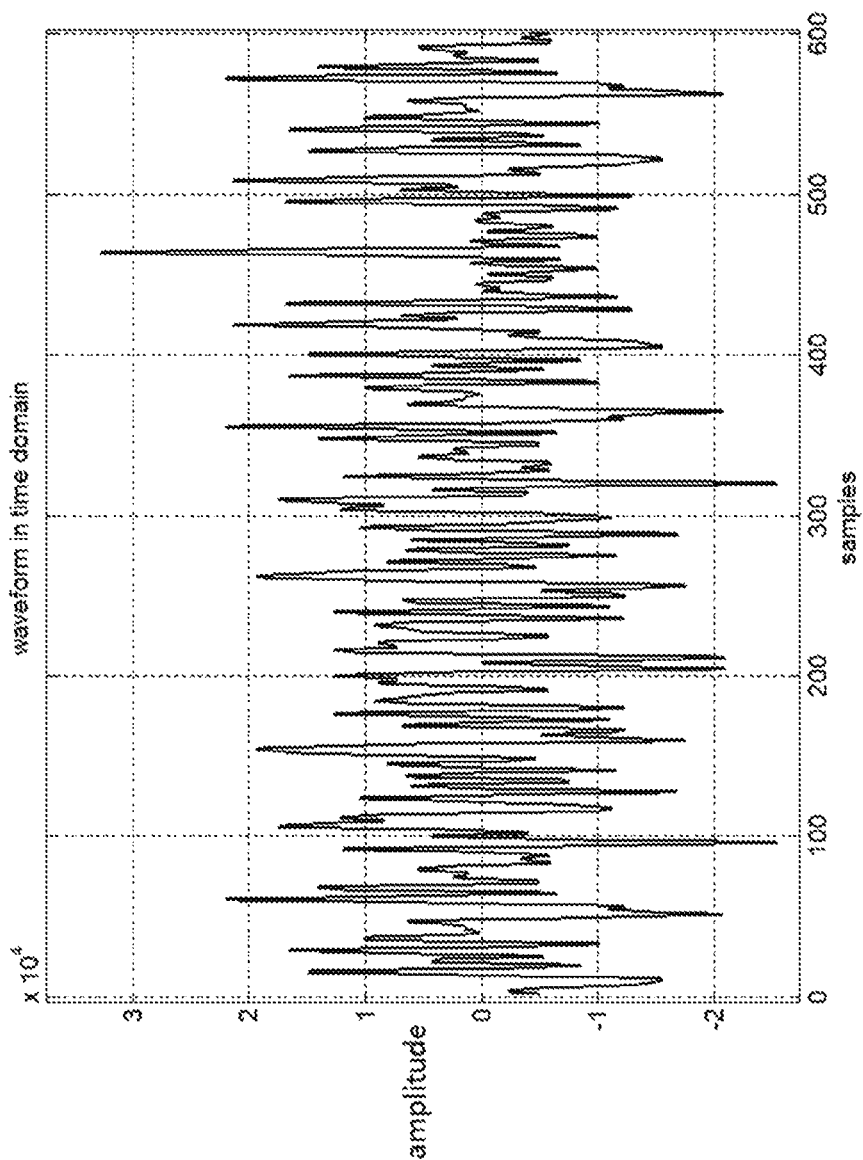
FIG. 5 is a view of transmitted waveforms according to embodiments of the present invention.

Multiple alternating currents of different frequencies generated with IFFTs in accordance with the above-described system are synchronously turned into a digital sequence in the time domain on all complete sinusoidal cycles of different frequencies. All of the frequency signals are orthogonal to each other. The signals can then be upconverted into a longer sequence, but transmitted within the same time period. The sequence can be stored in a memory which can be output continuously or periodically by a digital controller or generated in a real-time style from a digital processor. The sequence is converted to an analog current signal by a DAC at fixed rates. In some embodiments, the DAC clock rates may be 100 KHz to 10 MHz. Higher clock rates will produce fewer quantization errors or distortions in the analog waveforms. FIG. 5 shows the transmitted waveforms in the digital domain. The DAC clock rate is 3.353 MHz. It has 16 bits. Multiple sine-waves are added together.

Figure 6:
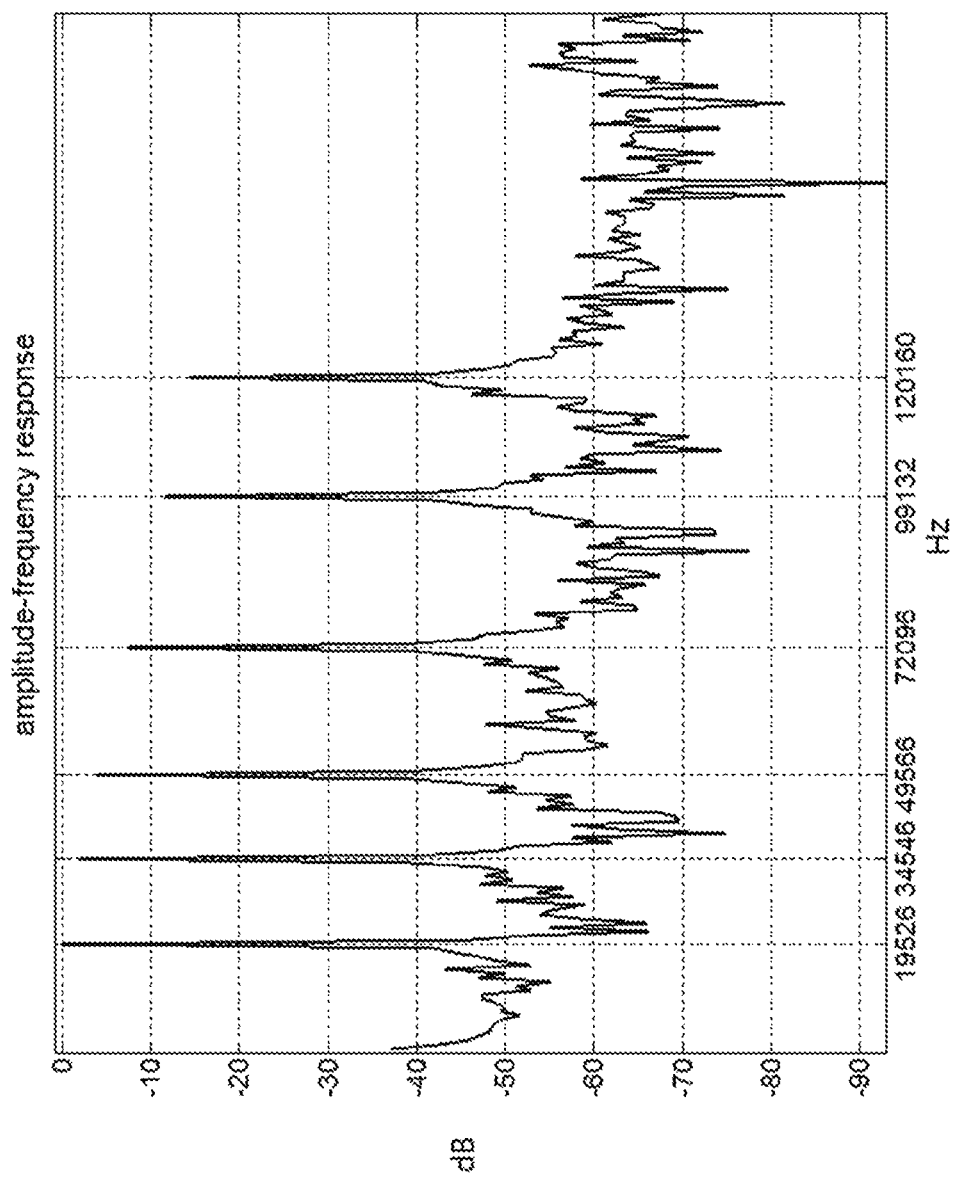
FIG. 6 is a view of the received signal's spectra according to embodiments of the present invention.
Figure 8:
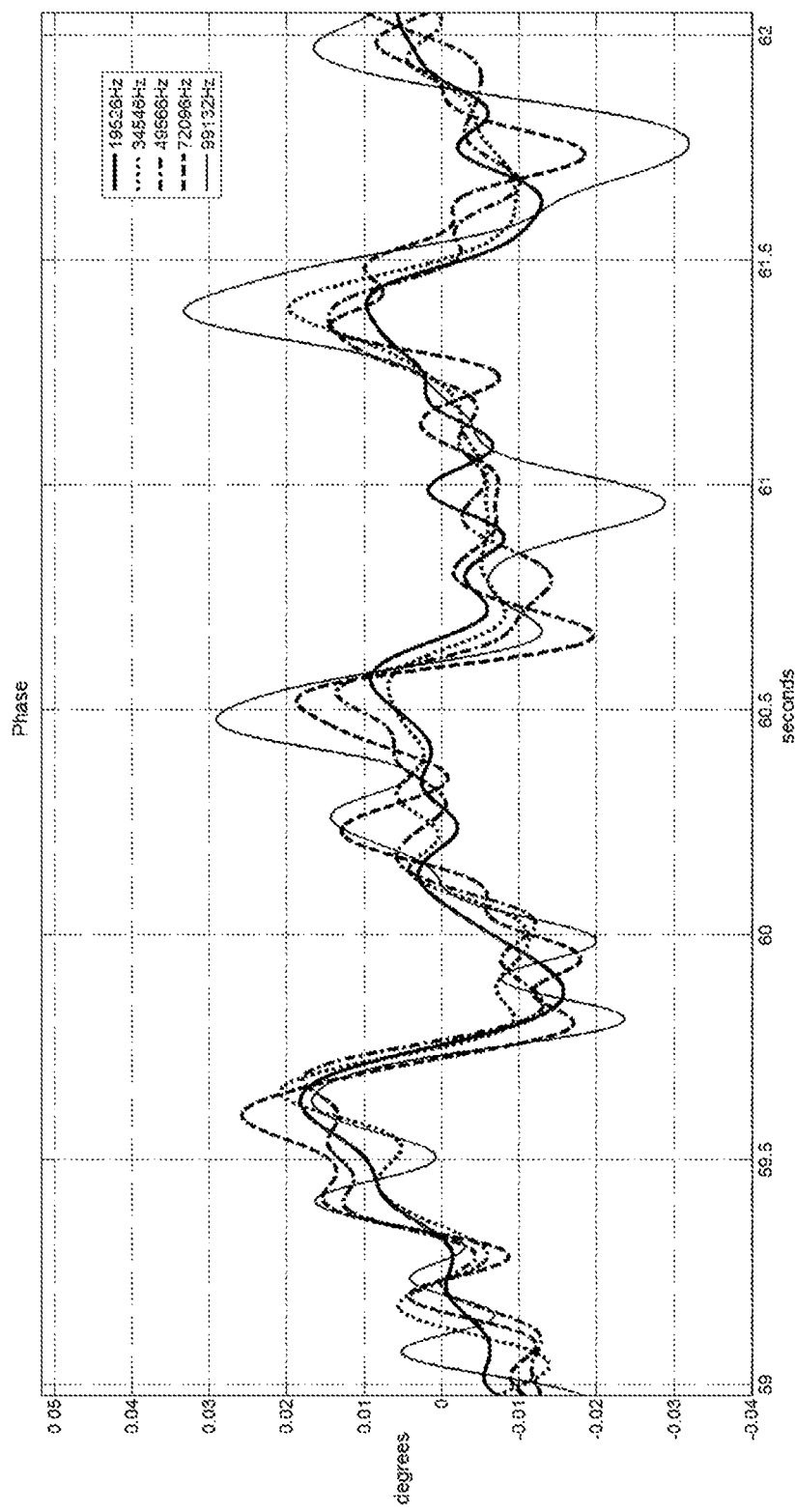
FIG. 8 is a view of phase curves of different frequencies according to embodiments of the present invention.

The multiple alternating currents are then injected into a human or animal body through electrodes and form a loop with external electrical parts. When the electrical currents are passing through the body, they are modulated by the body tissues and by changes in the tissues. And then sampled signals are obtained, and are synchronized according to the injected (transmitted) signals, and have the same time period. FIG. 6 shows the received signal's spectra. In one aspect, the ADC sampling rate is 769 KHz, and has 24 bits. Other sampling rates, and/or larger or smaller numbers of bits may be appropriate, depending on parameters to be measured, and other circumstances that ordinarily skilled artisans will appreciate. In one aspect, there are six sine-waves, which have frequencies of 19.5 KHz, 34.5 KHz, 49.6 KHz, 72.1 KHz, 99.1 KHz and 120 KHz. These sine-waves are travelling in the body and are modulated by the body; FIG. 8 shows phase curves having frequencies of 19.5 KHz, 34.5 KHz, 49.6 KHz, 72.1 KHz, and 99.1 KHz. They clearly show the cardiac cycles. Other numbers of frequencies, and/or other frequencies per se, may be selected, again depending on areas of the body for which measurements are desired, as ordinarily skilled artisans will appreciate.

The transmitting sequence and receiving sequence lengths shall not be necessarily the same, but the time periods must the same and synchronized. The sampled signal sequences are then demodulated with an FFT. All signals of different frequencies are extracted. Since the transmitted signals' phases are known, they can be subtracted from the extracted signals. The device's system amplitude and phase response can also be subtracted from the extracted signals. The final amplitudes and phases will represent the tissue modulations, which bring the physiological information. The signals are usually complex numbers because of modulation within the human or animal body. The complex signals provide the human or animal body information. The complex signals are processed, using low-pass filtering for example, to remove high-frequency noise. In one aspect, the cutoff frequency is usually around 10 Hz. A higher cutoff frequency will bring more details of waveforms, but may require a higher signal-to-noise ratio (SNR). In one aspect, embodiments of the present invention employ an adaptive low-pass filter. After the signal processing, the related information is extracted to calculate body fluid and blood flow parameters from different frequency signals. The results are frequency-compensated. The coefficients of equations to calculate physiological parameters are different. The cross-relationship of the results from different frequency currents are also examined. To get better results the same physiological parameters from different frequency signals can be summed with different weights. In the information extraction process, an electrocardiogram (ECG) is acquired as a cardio-timing reference. Blood pressure is measured separately along this processing. The specific acquiring processes and signal process are illustrated in FIGS. 2-4.

Figure 2:
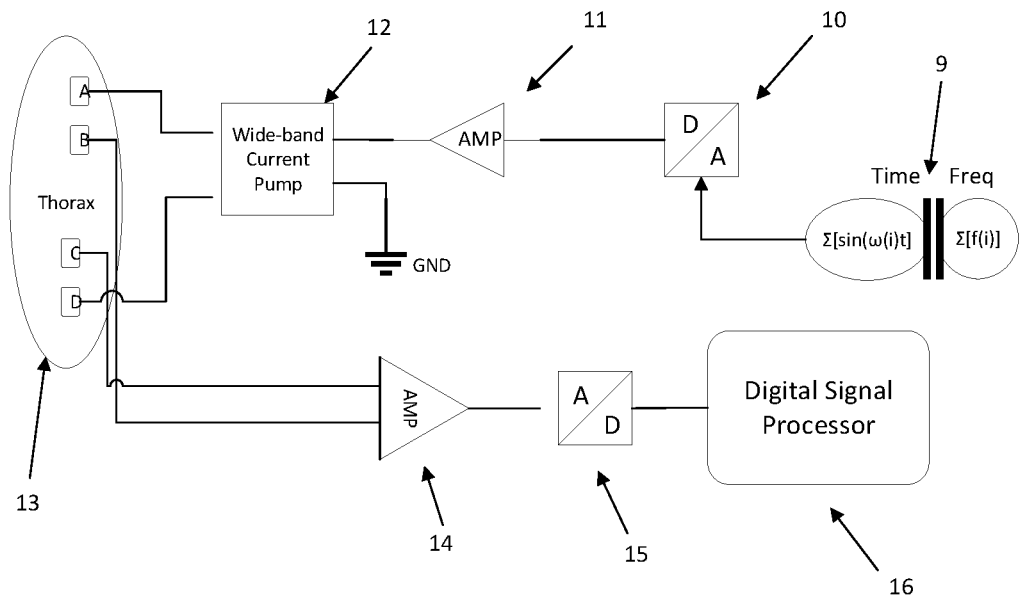
FIG. 2 is a structural view of the terminal system, according to embodiments of the present invention.

The terminal system shown in FIG. 2 is also called an acquisition system. Signal generator 9 can work both in the time domain and the frequency domain. The Figure also shows a digital-to-analog converter, 10, analog amplifiers 11 and 14, a wide-band current pump 12, an analog to digital converter 15, and a Digital Signal Processor (DSP) 16. In one aspect, the system not only acquires signals, but also sends stimulating currents into the human or animal body and tissues. Signal generator 9, which can work both in the time domain and the frequency domain, generates multi-frequency signals. In the time domain, the signals are the sum of multiple sine or cosine waves. In the frequency domain, the signals are the sum of multiple frequency "tones". It can transform the frequency "tones" into multiple sinusoidal signals in the time domain using IFFTs. The generated digital sinusoidal signals pass through a DAC 10 and become analog signals, which are amplified in analog amplifier 11 to drive a wide-band current pump 12 to do an impedance transform. Basically, current pump 12 transforms a wide-band single-ended voltage signal into a wide-band differential current signal. From current pump 12, a small current of multiple-frequency sinusoidal waves passes into the body via contacts A and D. The human or animal body, as a complex medium, will modulate the travelling current. This modulated current and other bio-electrical signals will be picked up from electrodes B and C. Since all of these signals are weak, they will be amplified by analog amplifier 14, and then will be digitized in ADC 15. The digitized signals will be processed by DSP 16, which pre-processes the digital signals by performing processes such as demodulation, filtering, extraction of different bio-signals, etc.

Figure 3:
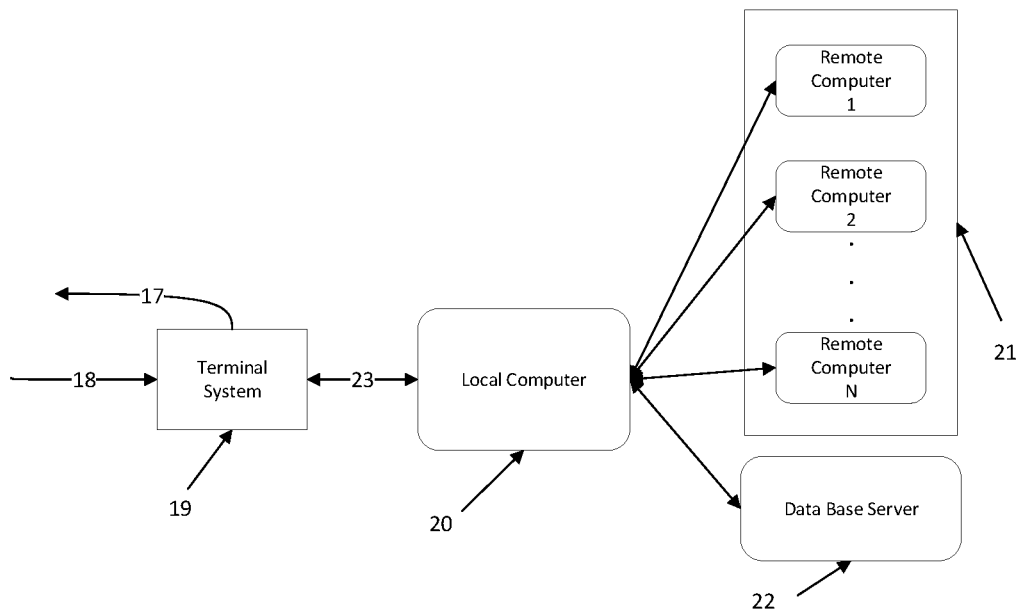
FIG. 3 is a schematic view of embodiments of the present invention.

FIG. 3 shows how the computer systems work in accordance with aspects of the present invention. Stimulating signals go out on path 17. Modulated signals and other bio-signals from a human or animal body are obtained on path 18. Terminal system 19 does some pre-processing work, including but not limited to exemplary functions such as demodulation and filtering. Terminal system 19 can also have its own human interface. Terminal system 19 sends out intermediate results to local computer 20, where all the final processing (such as parameter calculations, feature extractions, and data analyses) are done. Remote computers 21, using software in accordance with aspects of the invention, can get all information from the local computer 20 in a real-time manner or offline. The results and data can be stored in a data base server 22 anywhere, which can be retrieved from Local computer "20" and remote computers "21". "23" is the communication between the local host computer "20" and the terminal system "19".

Figure 4:
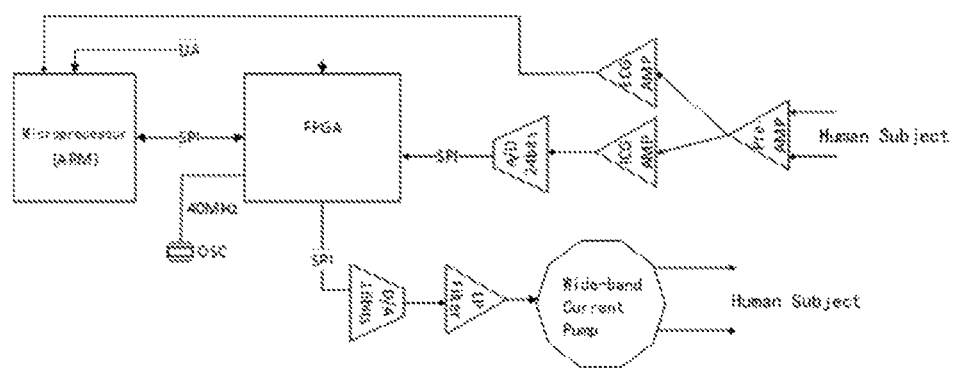
FIG. 4 is an internal structure view of the system according to embodiments of the present invention.
Figure 7:
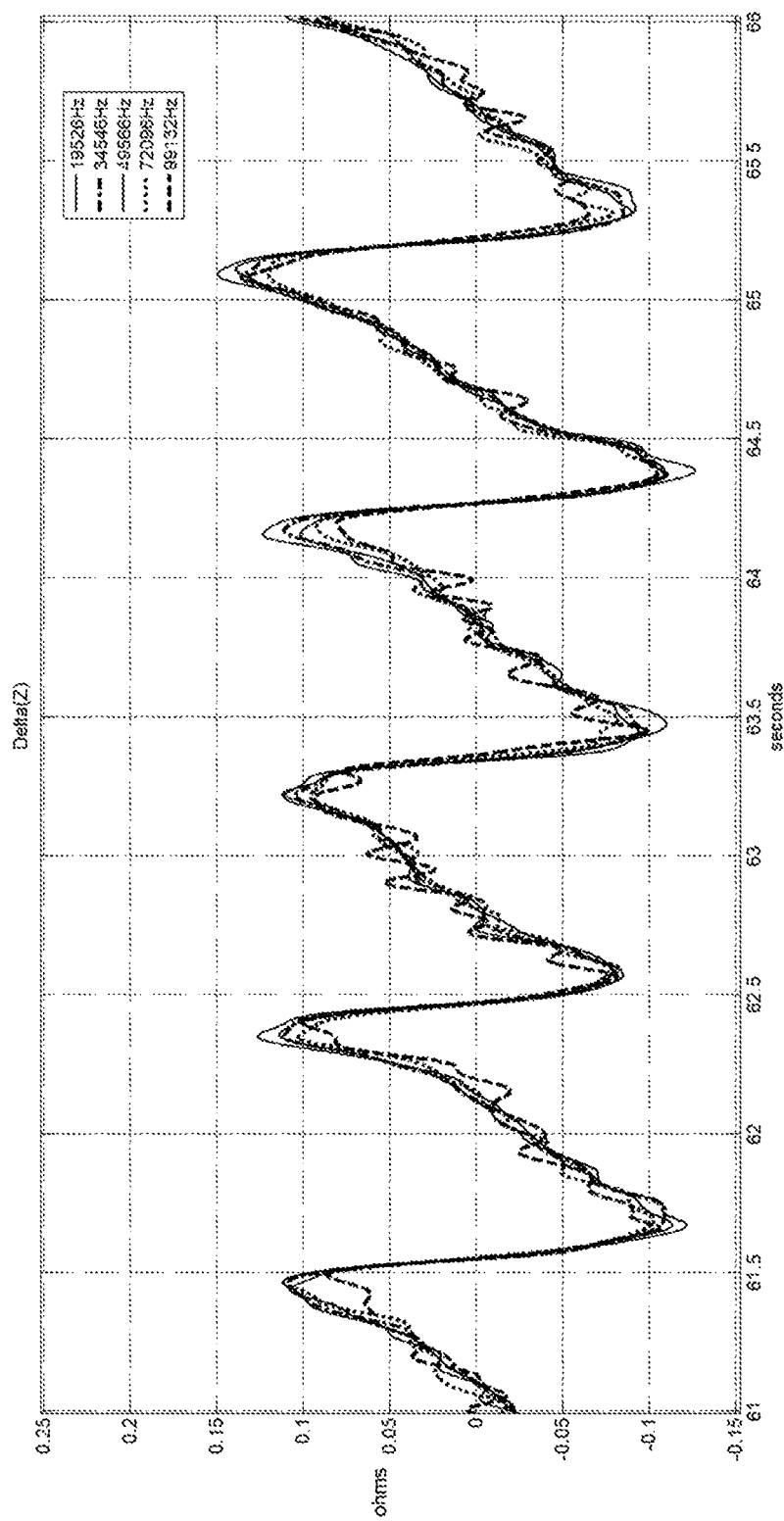
FIG. 7 is a view of a demodulated impedance cardiograph (ICG) according to embodiments of the present invention.
Figure 9:
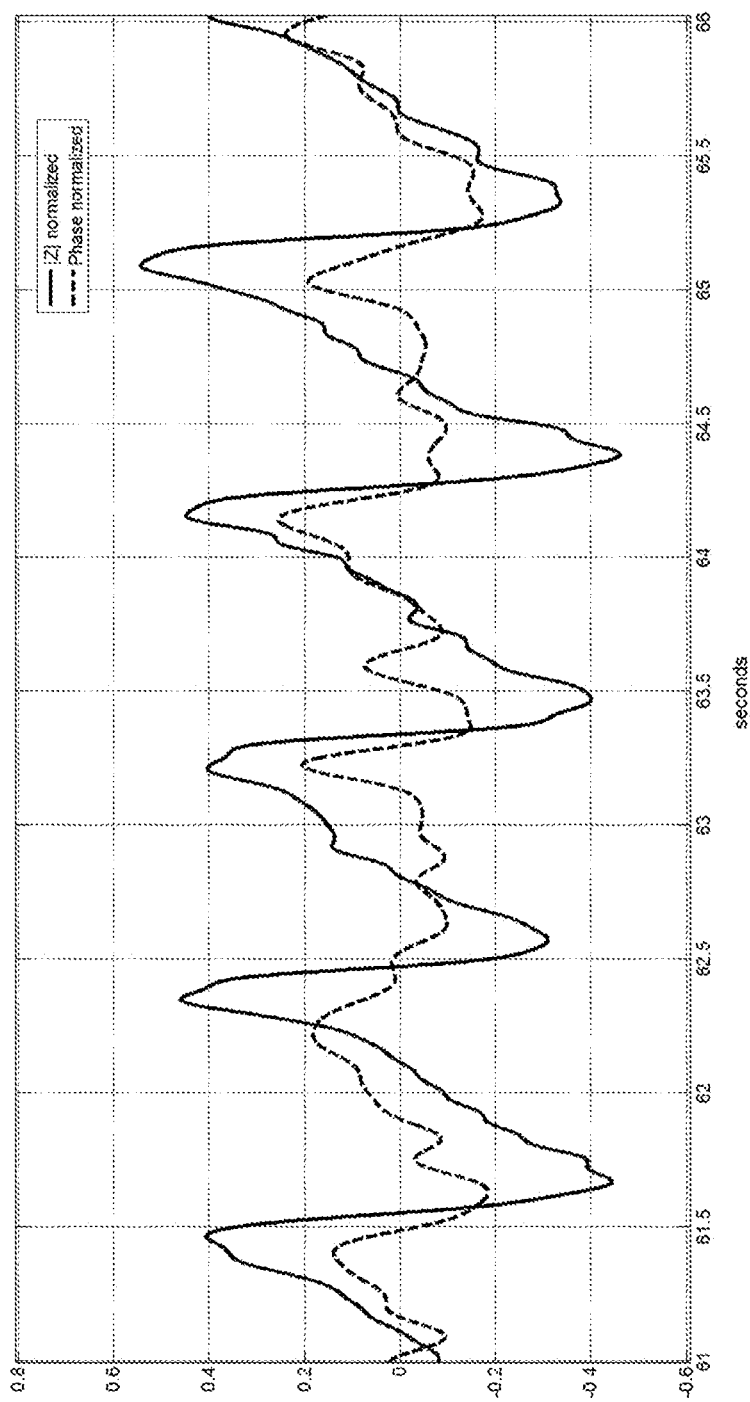
FIG. 9 is a view of the impedance amplitude and phase changes according to embodiments of the present invention.
Figure 10:
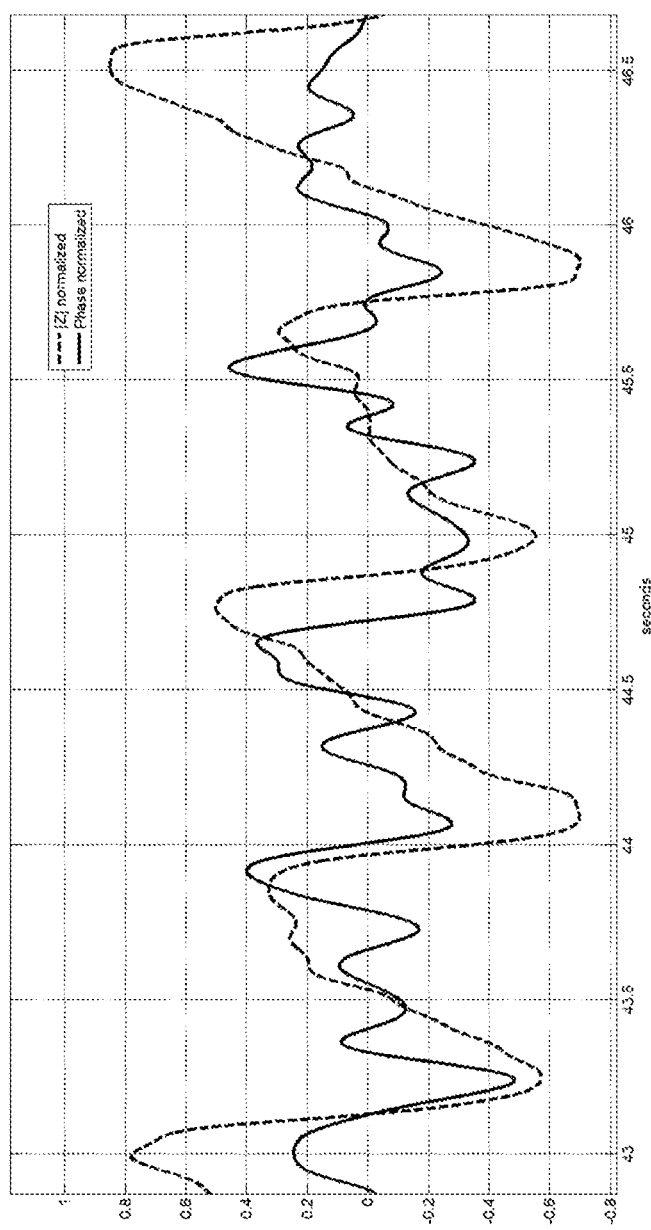
FIG. 10 is another view of the impedance amplitude and phase changes according to embodiments of the present invention.

FIG. 4 shows the terminal system or the acquisition system, including a microprocessor system (which in one aspect may include one or more ARM processors). Communication between the microprocessor system and peripheral components can be implemented by a field-programmable gate array (FPGA). Data are sent to the FPGA by the microprocessor and stored. The FPGA then can send the data to the DAC. The data are converted into an analog current signal to get an AC current input to a human or animal body. On the other hand, the preamplifier chooses to get an analog signal from the human or animal body system. A basic impedance transform is performed. The signal is input to two different amplifiers, one for impedance cardiography (ICG) and one for an electrocardiogram (ECG). ECG can be connected to the microprocessor system directly due to the microprocessor (ARM) having an ADC. An ICG signal can be digitized by a 24-bit ADC, and then transmitted to FPGA through a high-speed serial peripheral interface (SPI) bus. The FPGA re-packets the digital signal. The signal is transmitted to the microprocessor through another SPI bus and is demodulated by the microprocessor. FIG. 7 shows a demodulated ICG signal, corresponding to frequencies of 19.5 KHz, 34.5 KHz, 49.6 KHz, 72.1 KHz, and 99.1 KHz in one aspect. The cardiography signal, calculated from the received spectra, has five waveforms. Each ICG signal is calculated from one of five frequencies. The cardio-cycles are clearly shown here. FIGS. 9-10 show the impedance amplitude (ICG) and phase (reactance) changes through different human bodies. The Y-axis (without units) are normalized to 1.

Using the above-described system and the inventive method based on the measurement of bodily fluid, blood flow parameters and physiological parameters, the present invention provides a method and system monitoring hemodynamics of a human or animal, including bodily fluid and blood flow, including generating multiple synchronized alternating electrical currents (AC) of multiple frequencies simultaneously (in one aspect, the frequency range is from 10 KHz to 1 MHz), transferring the generated currents into a human or animal body, sensing the AC voltage changes caused by the human or animal body, amplifying and digitizing the sensed AC signals, processing the AC signals, estimating the hemodynamic parameters from the AC signals, and showing the parameter information in real-time on securely-connected computers in any location.

Based on the above-described measurement of bodily fluid, blood flow parameters, physiological parameters and the system for effecting such measurement, the present invention also provides a system/method to manipulate the extracted different information to obtain parameters about the human hemodynamics.

Based on the above-described measurement of bodily fluid, blood flow parameters, physiological parameters and the system for effecting such measurement, the present invention also provides a system/method to change the number of frequencies and the frequencies, and the intensities of AC currents.

Based on the above-described measurement of bodily fluid, blood flow parameters, physiological parameters and the system for effecting such measurement, the present invention also provides a system/method to detect the frequency dependencies of characteristics of human tissues and organs, such as conductivity and permittivity.

Based on the above-described measurement of bodily fluid, blood flow parameters, physiological parameters and the system for effecting such measurement, the present invention also provides a system/method to estimate a relationship between the frequency dependencies and the organ or tissue characteristics.

Based on the above-described measurement of bodily fluid, blood flow parameters, physiological parameters and the system for effecting such measurement, aspects of the present invention also provide a system/method to calculate hemodynamic parameters from frequency-dependent conductance and permittivity values. These parameters include but are not limited to, stroke volume (SV), cardiac output (CO), left ventricular ejection time (LVET), pre-ejection period (PEP), thoracic fluid content (TFC), acceleration index (ACI), velocity index (VI), heart rate (HR), systemic vascular resistance (SVR), and left cardiac work (LCW).

Throughout this description there are references to a human body or an animal body. The apparatus and method according to the present invention is equally applicable to both types. In addition, there are references throughout to various kind of parameters whose characteristics may be identified from the output of the inventive system and/or in accordance with the inventive method. Calculation of the individual parameters from signals at a single frequency is known. The use of multiple frequencies and multiple corresponding signals is what yields the superior results discussed earlier herein.

The descriptions of some embodiments are illustrative and exemplary, rather than enumerative or exhaustive. It is evident that many alternatives, modifications and variations will be apparent to those skilled in the art. Accordingly, it is intended to embrace all such alternatives, modifications and variations that fall within the spirit and broad scope of the appended claims.

Embodiments of the inventive method and apparatus to measure bodily fluid and its change, and blood volume change have been described in detail above. The specific examples illustrate the principle and implementation of the invention and assist in understanding the method and its core concepts. However, persons skilled in the art will appreciate that numerous variations and/or modifications may be made to the above-described embodiments, without departing from the broad general scope of the present disclosure. The present embodiments are, therefore, to be considered in all respects as illustrative and not restrictive.

The invention claimed is:

1. A method to measure bodily fluid parameters, blood flow parameters and physiological parameters, the method comprising:

summing multiple signals of different frequencies, synchronously aligning them on complete cycles of all frequencies and turning them into a digital sequence;

converting the digital sequence into multiple alternating currents, and transmitting the multiple alternating currents within a same time period;

injecting said multiple alternating currents as injecting signals into a human or animal body through electrodes and forming an injection loop with external electrical parts to produce modulated multiple alternating currents;

overlapping a receiving loop partially with the injection loop to sample the modulated multiple alternating currents as sampled electrical signals;

segmenting the sampled electrical signals into the same time period as that of transmitted sequences;

synchronizing the sampled electrical signals with said transmitted sequences;

demodulating the sampled electrical signals, and subtracting said injecting signals to produce final signals;

processing the final signals to calculate the bodily fluid parameters, blood flow parameters and/or physiological parameters from the multiple signals of different frequencies.

2. The method according to claim 1, wherein the summing is achieved by summing multiple signals of different frequencies in a frequency domain and synchronously turning the multiple signals of different frequencies into the digital sequence, the summing further comprising: summing the multiple signals of different frequencies in the frequency domain and synchronously turning the multiple signals of different frequencies into the digital sequence in a time domain on all complete sinusoidal cycles of different frequencies using an Inverse Fast Fourier Transform (IFFT).

3. The method according to claim 2, wherein the converting comprises passing the digital sequence through a Digital-to-Analog Converter (DAC) having clock rates from 100 KHz to 10 MHz.

4. The method according to claim 3, wherein the summing comprises upconverting the digital sequence into a longer sequence, but transmitting within the same time period.

5. The method according to claim 3, wherein when the modulated multiple alternating currents are passing through the human or animal body, they are modulated by blood and tissues within the human or animal body.

6. The method according to claim 3, further comprising analog-to-digital converting of the sampled electrical signals using a conversion rate between 100 KHz and 2.5 MHz.

7. The method according to claim 2, wherein the summing comprises upconverting the digital sequence into a longer sequence, but transmitting within the same time period.

8. The method according to claim 2, wherein when the modulated multiple alternating currents are passing through the human or animal body, they are modulated by blood and tissues within the human or animal body.

9. The method according to claim 1, wherein the summing comprises upconverting the digital sequence into a longer sequence, but transmitting within the same time period.

10. The method according to claim 9, wherein when the modulated multiple alternating currents are passing through the human or animal body, they are modulated by blood and tissues within the human or animal body.

11. The method according to claim 1, wherein when the modulated multiple alternating currents are passing through the human or animal body, they are modulated by blood and tissues within the human or animal body.

12. The method according to claim 11, further comprising extracting related information to perform the processing, wherein the related information comprises the human or animal body's impedance changes in amplitude and phase along a frequency range from 10 KHz to 1 MHz.

13. The method according to claim 12, further comprising monitoring states of the human or animal body using the calculated bodily fluid parameters, blood flow parameters and/or physiological parameters.

14. The method according to claim 1, wherein, after the overlapping, the method further comprises amplifying the detected sampled electrical signals and analog-to-digital converting the detected sampled electrical signals into digital signals.

15. The method according to claim 1, wherein the demodulating the sampled electrical signals further comprises, after subtracting the injecting signals from the sampled electrical signals to yield subtracted signals, subtracting system amplitude and phase responses from the subtracted signals.

16. A system for implementing the method of claim 1, wherein the system comprises a signal generator, a signal detector, and a signal processor;

the signal generator to generate the multiple signals of different frequencies and perform the summing and converting;

the signal detector to perform the injecting and overlapping to amplify collected bio-signals through wires or cables to produce the sampled electrical signals;

the signal processor to perform the segmenting, synchronizing, demodulating, and processing to extract bio-information from the final signals to calculate the bodily fluid parameters, blood flow parameters and/or the physiological parameters.

* * * * *